US012053239B2

(12) United States Patent
Costantini et al.

(10) Patent No.: US 12,053,239 B2
(45) Date of Patent: Aug. 6, 2024

(54) DEVICE, METHOD AND BOOTH FOR AUTOMATIC DETERMINATION OF THE SUBJECTIVE OCULAR REFRACTION OF A PATIENT

(71) Applicants: Florent Costantini, Paris (FR); Mathieu Costantini, Ajaccio (FR)

(72) Inventors: Florent Costantini, Paris (FR); Mathieu Costantini, Ajaccio (FR)

(73) Assignees: Florent Costantini (FR); Mathieu Constantini (FR)

( * ) Notice: Subject to any disclaimer, the term of this patent is extended or adjusted under 35 U.S.C. 154(b) by 607 days.

(21) Appl. No.: 17/055,455

(22) PCT Filed: Jun. 7, 2018

(86) PCT No.: PCT/FR2018/051326
§ 371 (c)(1),
(2) Date: Nov. 13, 2020

(87) PCT Pub. No.: WO2019/220023
PCT Pub. Date: Nov. 21, 2019

(65) Prior Publication Data
US 2021/0212560 A1    Jul. 15, 2021

(30) Foreign Application Priority Data
May 17, 2018   (FR) ..................................... 1854106

(51) Int. Cl.
*A61B 3/028*    (2006.01)
*A61B 3/032*    (2006.01)
(Continued)

(52) U.S. Cl.
CPC ............ *A61B 3/0285* (2013.01); *A61B 3/032* (2013.01); *A61B 3/02* (2013.01); *A61B 3/09* (2013.01); *A61B 3/10* (2013.01)

(58) Field of Classification Search
CPC ........ A61B 3/028; A61B 3/0285; A61B 3/032
(Continued)

(56) References Cited

U.S. PATENT DOCUMENTS 4,105,303 A * 8/1978 Guyton ................. A61B 3/036
351/247
5,914,772 A * 6/1999 Dyer ..................... A61B 3/028
351/222
(Continued)

FOREIGN PATENT DOCUMENTS

FR    3050922 A1    11/2017

OTHER PUBLICATIONS

International Search Report mailed Feb. 2, 2019, issued in corresponding International Application No. PCT/FR2018/051326, filed Jun. 7, 2018, 3 pages.
(Continued)

*Primary Examiner* — Zachary W Wilkes
(74) *Attorney, Agent, or Firm* — Christensen O'Connor Johnson Kindness PLLC

(57) ABSTRACT

A device, method and booth for automatic determination of the subjective ocular refraction of a patient. The device, which is preferably set up in a booth, has an automatic refractor, a central unit, a data input unit, an instruction-generating system controlled by the central unit and configured to generate instructions to the patient at least during an eye test, an interface system provided between the patient and the central unit and configured to detect, and to transmit directly to the central unit, indications generated in the form of gestures by the patient at least during an eye test, the central unit being configured to automatically perform at least one eye test, by controlling the automatic refractor and by receiving indications generated by the patient by way of the interface system, and to automatically determine, from (Continued)

these indications received, the subjective ocular refraction of the patient and/or a prescription for spectacles.

19 Claims, 5 Drawing Sheets

(51) Int. Cl.
  *A61B 3/02* (2006.01)
  *A61B 3/09* (2006.01)
  *A61B 3/10* (2006.01)
(58) Field of Classification Search
  USPC .................................................. 351/222, 223
  See application file for complete search history.

(56) References Cited

U.S. PATENT DOCUMENTS

| | | | |
|---|---|---|---|
| 2006/0023163 A1* | 2/2006 | Foster | A61B 3/18 351/205 |
| 2009/0153796 A1 | 6/2009 | Rabner | |
| 2013/0339043 A1* | 12/2013 | Bakar | A61B 3/185 705/2 |
| 2014/0129259 A1* | 5/2014 | Seriani | A61B 3/0033 705/3 |
| 2015/0070650 A1 | 3/2015 | Seriani | |
| 2015/0150446 A1 | 6/2015 | Park et al. | |
| 2016/0310000 A1 | 10/2016 | Meneghini | |
| 2017/0329154 A1 | 11/2017 | Liang | |

OTHER PUBLICATIONS

Written Opinion of the International Searching Authority mailed Feb. 2, 2019, issued in corresponding International Application No. PCT/FR2018/051326, filed Jun. 7, 2018, 7 pages.
Written Opinion of the International Searching Authority mailed Feb. 2, 2019, issued in corresponding International Application No. PCT/FR2018/051326, filed Jun. 7, 2018, 5 pages.
International Preliminary Report on Patentability mailed Nov. 17, 2020, issued in corresponding International Application No. PCT/FR2018/051326, filed Jun. 7, 2018, 1 page.

* cited by examiner

DEVICE, METHOD AND BOOTH FOR AUTOMATIC DETERMINATION OF THE SUBJECTIVE OCULAR REFRACTION OF A PATIENT

CROSS-REFERENCE TO RELATED APPLICATIONS

This application is a National Stage of International Application No. PCT/FR2018/051326, filed Jun. 7, 2018, which claims priority to French Patent Application No. 1854106, filed May 17, 2018, the entire disclosures of which are hereby incorporated by reference in their entirety for all purposes.

TECHNICAL FIELD

The present invention relates to a device and a method for the automatic determination of the subjective ocular refraction of a patient, as well as a booth equipped with such a device.

Ocular refraction is the change of direction of a light ray that passes through different media in the eye. This ray ultimately converges on the retina, that is to say on the layer of cells that line the bottom of the eyeball and which is intended to transform light energy into nerve impulses that are then decoded by the brain in the form of images.

Ocular refraction is used to determine abnormalities in the vision (ametropia) of a person (hereinafter referred to as the "patient"). The ametropias of an eye are defined by the position of the light rays entering the eye, which are deflected in relation to the retina. Depending on the position of these rays, the eye is considered myopic, normal or hypermetropic. In addition, when light rays describe a surface on the retina instead of a point, the eye is astigmatic.

STATE OF THE ART

To determine the ocular refraction of a patient, an automatic refractometer (or "auto-refractometer") is generally used to measure a theoretical refraction called objective refraction, which defines an objective correction for each of the patient's eyes.

However, since the condition of a patient's eyes may vary over time, the results provided by an automatic refractometer are variable over time. Muscular and neurosensory phenomena such as accommodation can also cause these results to vary. Thus, during an ophthalmological examination or consultation, in particular with a view to prescribing corrective lenses adapted to the patient, the ophthalmologist (or another vision professional such as an orthoptist, optometrist or optician) determines the subjective ocular refraction of the patient, requiring the patient's participation.

The eye care professional (ophthalmologist, orthoptist, optometrist or optician for example) usually uses an automatic refractor to do this. An automatic refractor typically consists of an ocular device with two eyepieces to be placed in front of the patient's eyes, a management unit configured to take corrective lenses from a supply and position them in the eyepieces, and a control interface that is used by the eye care professional to operate the management unit. During this examination, different combinations of corrective lenses are placed in the eyepieces, and the patient checks, by looking at a target through the ocular device, whether the lens or lenses presented allow a clear view of the target.

The eye care professional generally has to perform a large number of successive tests before being able to determine a comfortable vision correction for the patient. Such an examination is therefore takes a significant amount of time.

FR 3 050 922 discloses a method for reducing the duration of an examination of the subjective ocular refraction of a patient. This method, whose aim is to control an automatic refractor, is characterised by a step of the determination of an accommodative profile indicating a capacity of the eye to accommodate excessively or not, and a step of generation of at least one selection command identifying corrective lenses to be successively positioned in the ocular device in order to subject the eye to several successive refractive tests, wherein the selection command depends on the accommodative profile determined. This method enables the automatic determination of a set of tests by identifying corrective lenses to be positioned in the ocular device, thus reducing the duration of the examination.

However, during the examination eye tests are always performed in the usual way. In particular:
the patient is guided by an operator such as an eye care professional who controls the conduct of the test(s) (determined automatically); and
the operator enters the responses provided by the patient into the system during testing.

This method, although partially automated, still requires the intervention of an operator, usually an eye care professional, which has drawbacks especially in terms of cost and availability.

DESCRIPTION OF THE INVENTION

The present invention provides a device for the automatic determination of at least the subjective ocular refraction of a patient. It concerns a device comprising:
an automatic refractor comprising an ocular device (with one or two eyepieces) and a management unit configured to take corrective lenses from a reserve and position them in the ocular device;
a central unit configured to at least control the automatic refractor management unit to position corrective lenses in the ocular device; and
a data input unit for entering at least patient-related data into the central unit.
According to the invention:
said device further comprises:
an instruction generation system controlled by the central unit and configured to automatically generate instructions to the patient at least during an eye test; and
an interface system between the patient and the central unit, which is configured to detect, directly, indications generated in the form of gestures, preferably manually, by the patient at least during an eye test and to transmit these indications directly to the central unit; and
the central unit is also configured to automatically implement at least one eye test, by controlling the management unit and receiving the indications generated by the patient via the interface system, and to automatically determine the subjective ocular refraction from at least said received indications.

The central unit is preferably configured to generate a prescription comprising a prescription for spectacles for the patient, adapted to the subjective ocular refraction thus determined.

In the context of the present invention, the term "direct" detection and/or transmission of gestural indications (or indications generated in the form of gestures) means the detection without the intervention of a third party (such as an operator, in particular an eye care professional) of these gestural indications and the transmission of these gestural indications to the central unit of the device, also without the intervention of a third party.

Thus, thanks to the simultaneous automatic generation of instructions to the patient (via the instruction generation system) with a view in particular to the conduct of one or more eye tests, and the direct detection and taking into account of the patient's responses (expressed in the form of gestures) during this or these eye tests (via the interface system), this device does not require the intervention of an operator, such as an eye care professional, to perform the necessary eye test(s) at the central unit of the device to determine the subjective ocular refraction of the patient. Simply by collaborating with the patient, without the intervention of a third party (such as an operator), this device thus makes it possible to automatically determine the subjective ocular refraction of the patient and to automatically generate a prescription where necessary, which brings advantages in particular in terms of cost and availability and makes it possible to remedy the aforementioned drawbacks.

Advantageously, the said device comprises, in addition, at least one of the following elements:
  a recording element configured to record the prescription; and
  a print element configured to print the prescription.

Moreover, in a particular embodiment, the device also comprises a transmission element configured to transmit the prescription remotely to a user.

In addition, in a preferred embodiment, the instruction generation system comprises a voice output unit.

In the context of the present invention:
  the interface system is a system which makes it possible to automatically detect the patient's gestures, which they perform in order to provide (or generate) the said indications (gestures), which represent their comments (or responses) relating to the questions asked during the eye test(s);
  the patient's gestures correspond to movements of at least one part of their body. These movements preferably concern movements or actions performed by one or both hands of the patient. However, the use of other parts of the body, such as, for example, the feet, may be considered in the context of the present invention.

In a first embodiment, the interface system comprises at least one manual actuating element. This manual actuating element is configured to be manually operated by the patient. This may include one or more actuating elements such as buttons. It can also be a joystick. In this first embodiment, the indications in the form of gestures thus represent manual actuations of the manual actuating element.

In addition, in a second embodiment, the interface system comprises a system for automatic detection of patient gestures. In this second embodiment, the indications (in the form of gestures) represent gestures, in particular movements of one or both hands, which are detected automatically and directly by the said automatic gesture detection system (and transmitted to the central unit).

Moreover, in a particular embodiment, the said device comprises, in addition:
  an automatic refractometer configured to measure the objective ocular refraction of the patient and to transmit it to the central unit, wherein the measured objective ocular refraction is used by the central unit to perform at least one of the following two actions: generate said at least one eye test, determine said subjective ocular refraction; and/or
  a frontofocometer configured to measure the spectacle lenses corrections of the patient and to transmit the measured corrections to the central unit, wherein the measured corrections are used by the central unit to perform at least one of the following two actions: generate said at least one eye test, determine said subjective ocular refraction; and/or
  a voice control system allowing the patient to provide the device with voice indications.

Within the framework of the present invention, the various components (and in particular the automatic refractor, the central unit, the data acquisition unit, the instruction generation system and the interface system, as well as the automatic refractometer and the frontofocometer, as the case may be) of the device may be connected together in different ways, in order to communicate and transmit data and/or commands in particular.

Thus, advantageously:
  in a first embodiment, said device comprises a local network configured to allow communications between at least some of said elements of said device;
  in a second embodiment, at least some of said elements of said device communicate with one another via serial links; and
  in a third embodiment, at least some of the said elements of the said device communicate with each other by means of a wireless (or "wifi") communication.

The present invention also relates to a booth for automatic determination of the subjective ocular refraction of a patient (and preferably for generation of a prescription).

According to the invention, said booth is at least partially closed and comprises at least one seat for a patient and a device for automatic determination of the subjective ocular refraction of a patient as specified above.

Advantageously, the various elements (of the said device for automatic determination of the subjective ocular refraction) are arranged in the booth in such a way that they are accessible, if necessary, from the patient's seat.

The present invention further concerns a method for automatic determination of the subjective ocular refraction of a patient, by means of a device such as the aforementioned one, which comprises at least:
  an automatic refractor comprising an ocular device and a management unit configured to take corrective lenses from a reserve and position them in the ocular device;
  a central unit;
  a data input unit;
  an instruction generation system; and
  an interface system between the patient and the central unit.

According to the invention, the said method comprises:
  a generation step, implemented by the central unit, and consisting of automatically generating at least one eye test, using at least inputted data relating to the patient;
  a test step consisting of implementing at least one eye test generated in the generation step, the test step comprising at least:
  a sub-step of generation of instructions for the patient, implemented by the instruction generation system;
  a sub-step of controlling the automatic refractor management unit to take corrective lenses from the reserve and position them in the ocular device;
  a sub-step of direct detection of indications generated in the form of gestures by the patient during the eye test, by looking at displays through the ocular device, and direct transmission of these indications to the central unit, implemented by the interface system; and a processing step, implemented by the central unit, and consisting of automatically determining the subjective ocular refraction of the patient, from at least the said indications received, as well as a prescription.

The said process advantageously also comprises at least one data input step, which is implemented prior to the generation step.

The generation and testing steps preferably use a fog test.

In addition, in a preferred embodiment, the test step consists of displaying letter Es with branches with different orientations, which can be easily and simply recognised, especially by populations of illiterate individuals.

BRIEF DESCRIPTION OF THE DRAWINGS

The invention will be better understood, and the other purposes, details, characteristics and advantages of the invention will appear more clearly in the following detailed explanatory description of the embodiments of the invention given as a purely by way of a illustrative and non-exhaustive example, with reference to the attached schematic drawings. In these drawings.

DETAILED DESCRIPTION

Figure 1:
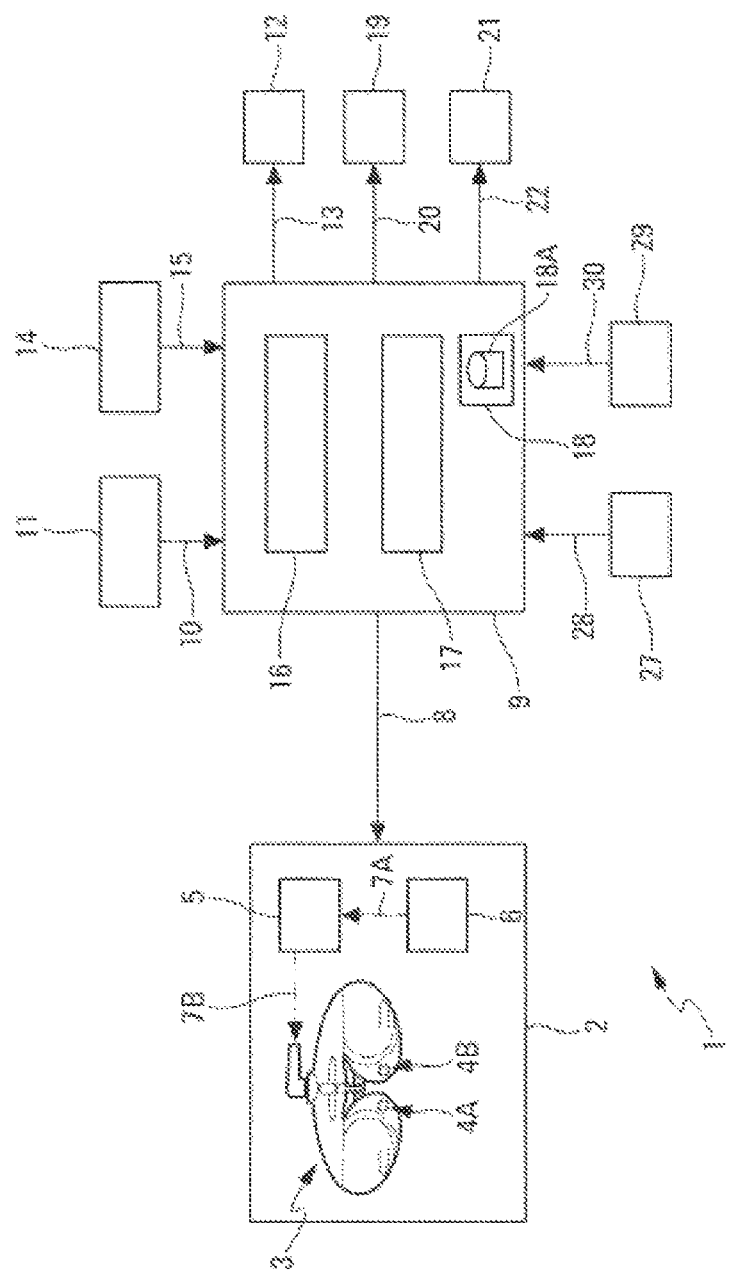
FIG. 1 is a synoptic diagram of a particular embodiment of an inventive device for determination of the subjective ocular refraction of a patient.

Device 1, shown schematically in FIG. 1 and serving to illustrate the present invention, is a device for automatic determination of at least the subjective ocular refraction of a patient.

This device 1 usually comprises:
- an automatic refractor 2 comprising an eyepiece device 3 provided with one or preferably two eyepieces 4A and 4B and a management unit 5 configured to take corrective lenses from a reserve 6 for example using an articulated arm (not shown) and position them in the eyepieces 4A and 4B, as shown schematically by mixed lines 7A and 7B in FIG. 1;
- a central unit 9 configured to at least control the management unit of the automatic refractor 2, as illustrated by link 8, in order to position lenses in the eyepiece(s) 4A and 4B of the eyepiece device 3; and
- a data input unit 11 for inputting at least patient-related data into the central unit 9 as illustrated by a link 10.

The data input unit 11 can comprise any type of element or usual means of inputting data, such as for example a keyboard associated with a screen or a touch screen.

According to the invention, said device 1 further comprises:
- an instruction generation system 12 controlled by central unit 9, as illustrated by a link 13, and configured to generate instructions to the patient at least during an eye test; and
- an interface system 14 creating an interface between the patient and the central unit 9.

According to the invention, the interface system 14 is configured to detect, directly, indications generated by the patient in the form of gestures, and preferably in manual form, at least during an eye test, and to transmit these detected indications (in the form of gestures) directly to central unit 9 via a link 15.

In addition, according to the invention, central unit 9 comprises a control element 16 which is configured:
- to automatically implement at least one eye test, by controlling management unit 5, by guiding the patient via instruction generation system 12 and receiving the indications generated by the patient via interface system 14; and
- to automatically determine the subjective ocular refraction from at least said received indications.

Central unit 9 also comprises a processing element 17 configured to generate a prescription. This prescription comprises, in particular, a prescription for corrective lenses of spectacles for the patient, whose correction is adapted to the subjective ocular refraction determined by control element 16.

Said device 1 also comprises a recording element 18 which is configured to record at least the prescription (and possibly the objective ocular refraction) generated by processing element 17, on a storage medium 18A, internal or external (to central unit 9), of any usual type, for example a USB key.

Additionally and/or alternatively, device 1 comprises a printing element (or printer) 19. This printing element 19 is configured to print on paper the prescription generated by processing element 17 (or simply the subjective ocular refraction) and received via a link 20. Thus, immediately after the examination, the patient will have a prescription in the form of a paper document, allowing them to obtain spectacles adapted to their vision.

Furthermore, in a special embodiment, device 1 comprises, additionally and/or alternatively, a transmission element 21. This transmission element 21 is configured to transmit (in particular remotely via the Internet) the prescription, generated by processing element 17 (or simply the subjective ocular refraction) and received via a link 22, to a user, for example a healthcare professional.

Thus, device 1 is able to perform a teletransmission of the prescription and/or subjective ocular refraction.

In a preferred embodiment, the instruction generation system 12 comprises a conventional voice output unit, comprising a loudspeaker 31 (FIGS. 2 and 3), which is configured to generate the instructions as voice signals, i.e. via a synthesised voice. One of the purposes of these instructions is to guide the patient, especially when performing eye tests, as described below. Alternatively, it is also possible for the instruction generation system 12 to generate the instructions in visual form.

In the context of the present invention:
- the interface system 14 is a system which makes it possible to automatically detect the gestures of the patient, i.e. the gestures which the patient performs to provide (or generate) the said indications (in the form of gestures), which represent their comments (or responses) relating in particular to questions asked during an eye test;

the gestures of the patient correspond to movements of a part of the body of said patient. Preferably, these movements concern movements or actions performed by one or both hands of the patient. However, movements of other parts of the body of the patient may be envisaged in the context of the present invention, such as, in particular, movements of the feet of the patient which act, for example, on pedals or other mechanical elements (in this case forming part of interface system 14).

Figure 2:
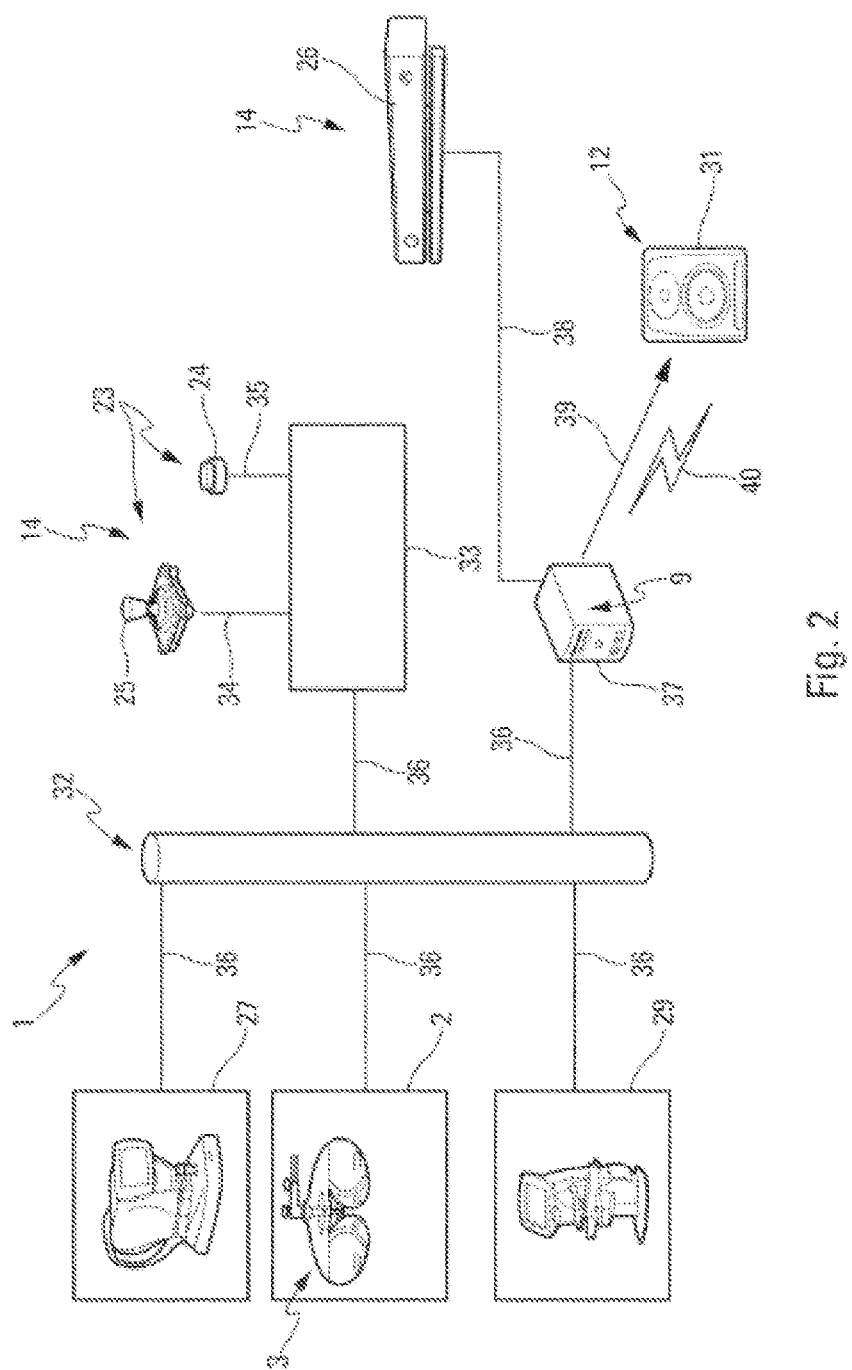
FIG. 2 schematically shows a first mode of communication between different elements of the device, via a local network.
Figure 3:
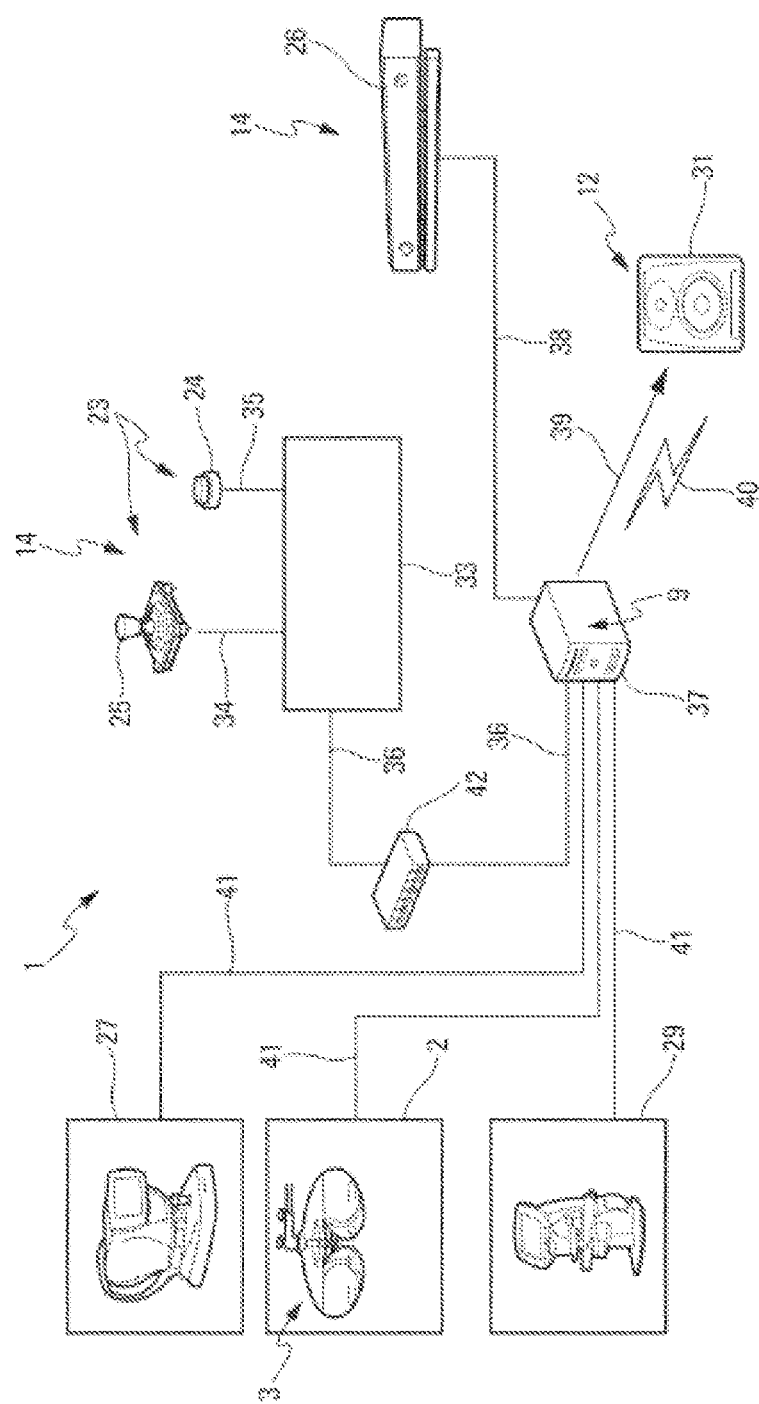
FIG. 3 schematically shows a second mode of communication between different elements of the device, via serial links.

In a first embodiment, interface system 14 comprises at least one manual actuating element 23. This manual actuating element 23 is configured to be manually operated by the patient. In particular, this may be one or more actuating elements such as buttons, e.g. pushbuttons or rotary knobs, as shown for example in FIGS. 2 and 3 with button 24. By way of illustration, manual actuating element 23 can comprise two buttons, one of which indicates the right and the other the left, for example. Manual actuating element 23 can also be a conventional joystick 25, as shown in FIGS. 2 and 3. For example, such a joystick 25 can be moved in two different directions, forwards/backwards and up/down. In this first embodiment, the indications in the form of gestures thus represent manual actuations of manual actuating device 23 by the patient.

In addition, in a second embodiment, interface system 14 comprises a detection system 26 (FIGS. 2 and 3) of the usual type, which is configured to automatically detect (remotely, i.e. without contact) the gestures of the patient. In this second embodiment, indications in the form of gestures represent gestures, in particular movements of one or both hands of the patient, which are detected automatically and directly by detection system 26 without the intervention of a third party and without contact with the patient.

Furthermore, in a particular embodiment, device 1 comprises a voice command system (not shown) that allows the patient to provide said device 1 (and in particular central unit 9) with indications in vocal form, especially during an eye test.

Furthermore, in a preferred embodiment, said device 1 also comprises, as shown in FIG. 1, a conventional automatic refractometer 27 configured to measure the objective ocular refraction of the patient. To perform this examination, the patient must rest their forehead and chin against and upon appropriate supports. Automatic refractometer 27 then automatically measures the objective ocular refraction of the eyes of the patient. Automatic refractometer 27 is configured to automatically transmit to central unit 9, via a link 28, the objective ocular refraction thus measured. This measured objective ocular refraction is used by central unit 9 to automatically generate the eye test(s) and/or to automatically determine said subjective ocular refraction.

Moreover, in a particular embodiment, said device 1 comprises, in addition, as shown in FIG. 1, a usual frontofocometer 29 configured to measure the corrections of the lenses of the spectacles of the patient. In a preferred embodiment, frontofocometer 29 is automated. This frontofocometer 29 is configured to transmit the measured corrections to central unit 9 via a link 30. These measured corrections are used by central unit 9 to automatically generate the eye test(s) and/or to automatically determine said subjective ocular refraction.

Within the framework of the present invention, the various components (and in particular automatic refractor 2, central unit 9, data input unit 11, instruction generation system 12 and interface system 14, as well as, where appropriate, automatic refractometer 27 and frontofocometer 29) of device 1 can be connected together in different ways, in order to communicate and transmit data and/or commands in particular.

In a first embodiment, shown in FIG. 2, device 1 comprises a Local Area Network (LAN) that is configured to allow communications between at least some of the above-mentioned elements of device 1.

In the example of FIGS. 2 and 3, interface system 14 comprises a nanocomputer 33 equipped with an ARM processor, e.g. of the Raspberry PI type. Button 24 and joystick 25 are each connected to nanocomputer 33 via a USB link or a Raspberry PI IO bus, i.e. a set of electronic connections between the different units (inputs or outputs) of the Raspberry PI electronic board, as illustrated by links 34 and 35.

In the example shown in FIG. 2, automatic refractor 2, central unit 9, nanocomputer 33, automatic refractometer 27 and frontofocometer 29 are linked (or connected) to local network 32 via usual connectors 36, for example of the RJ45 type.

In addition, in the two embodiments of FIGS. 2 and 3, central unit 9 which is, for example, integrated in a computer 37 is linked to detection system 26 via a link 38, for example of the USB type. In addition, central unit 9 is linked to instruction generation system 12 via a wired link 39 ("jack" or "RCA" outlet) or a "Bluetooth" type link 40.

In addition, in a second embodiment, shown in FIG. 3, at least some of the elements of device 1 communicate with each other via serial links 41. By way of illustration, in the example shown in FIG. 3, automatic refractor 2, automatic refractometer 27 and the frontofocometer 29 are linked (or connected) to central unit 9, via such links 41, for example RS232 links of the UART ("Universal Asynchronous Receiver Transmitter") type.

In this second embodiment, device 1 also comprises a device 42 of the "HUB" or "Switch" type, which connects via connectors 36, e.g. of the RJ45 type, the nanocomputer 33 of the interface system 14 to the central unit 9.

In addition, in a third embodiment (not shown), at least some of the elements of device 1 communicate with each other via wireless (or "wifi") communication.

Figure 4:
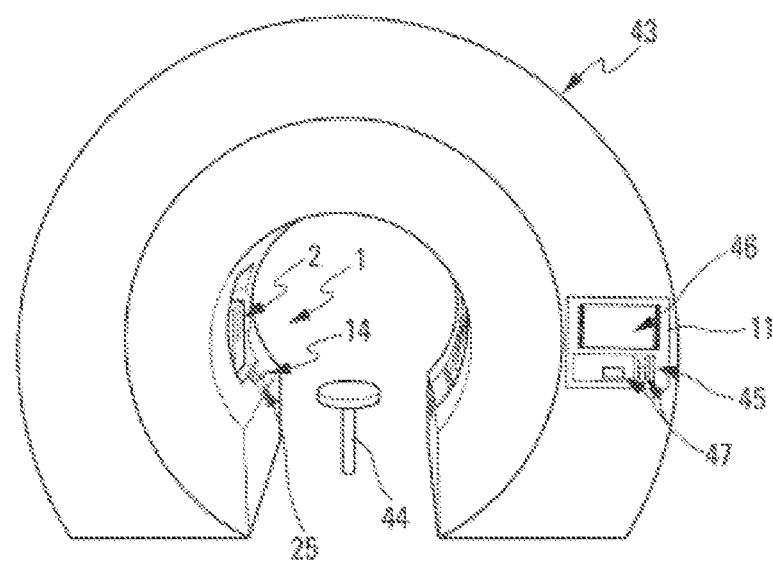
FIG. 4 is a schematic perspective view of a booth for determination of the subjective ocular refraction of a patient.
Figure 5:
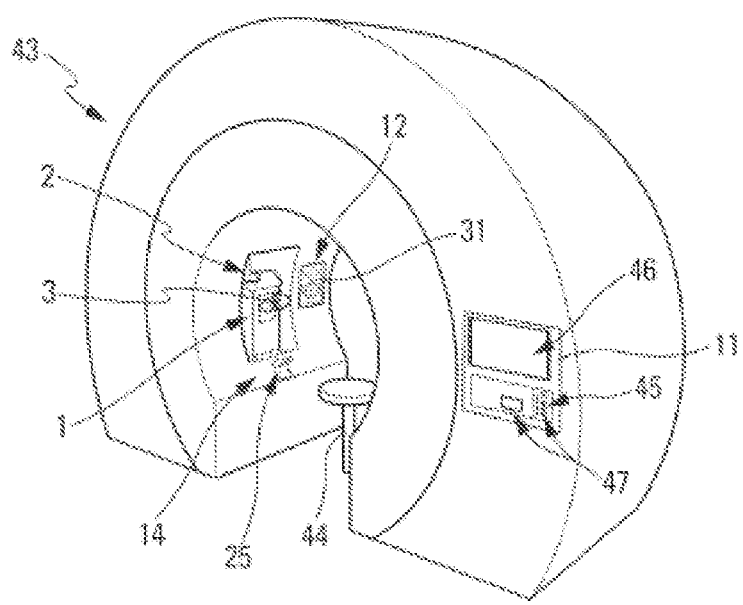
FIGS. 5 and 6 are schematic perspective views, looking respectively from the right and left, of the booth in FIG. 4.
Figure 6:
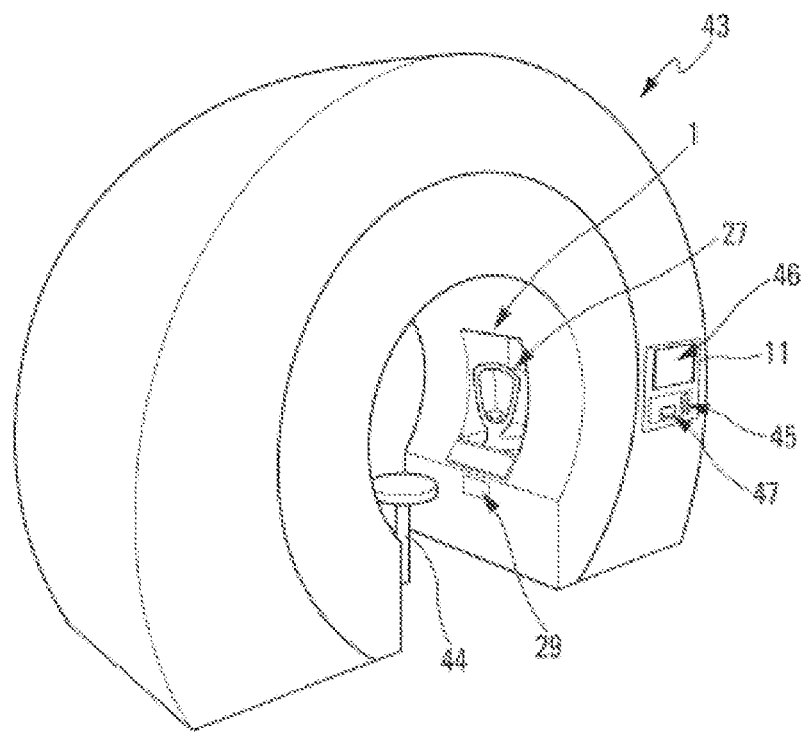

In a preferred application, represented in FIGS. 4 to 6, device 1 for automatic determination of the subjective ocular refraction of a patient, as described above, is integrated in a booth 43 (for automatic determination of subjective ocular refraction). This booth 43 is at least partially closed and comprises, in addition to device 1, a seat 44 for a patient. This seat 44 is adjustable, especially in height and possibly in the horizontal plane.

The various elements of the said device 1 and in particular automatic refractor 2, interface system 14, automatic refractometer 27 and frontofocometer 29 are arranged in such a way as to be accessible from the patient seat 44.

Automatic refractometer 27 and frontofocometer 29 can be optional in a simplified embodiment.

By way of illustration, data input unit 11, for example a keyboard 45 combined with a display 46, can be arranged at the entrance to booth 43, as shown in the example in FIGS. 4 to 6. Data input unit 11 can also be arranged inside booth 43. Data unit 11 can also comprise a payment terminal 47, for a payment, e.g. by credit card.

In the example shown, booth 43 comprises within it:
on one side, as shown in FIG. 5, automatic refractor 2, interface system 14, and instruction generation system 12; and
on the other side, as shown in FIG. 6, automatic refractometer 27 and frontofocometer 29.

Figure 7:
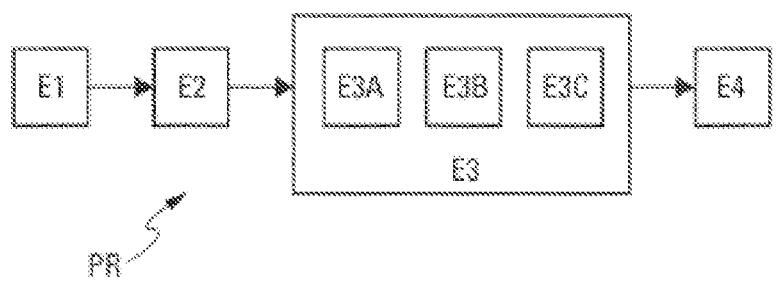
FIG. 7 schematically shows the main steps of a particular embodiment of a method for the automatic determination of the subjective ocular refraction of a patient.

A PR method for automatic determination of the subjective ocular refraction of a patient is described below, with reference to FIG. 7 in conjunction with FIG. 1, using a device 1 such as the one described above.

This PR method comprises:
- a data input step E1 consisting of inputting data relating to the patient into device 1 (and more particularly into the central unit 9);
- a generation step E2, implemented by central unit 9, and consisting of automatically generating at least one eye test, using at least inputted data, relating to the patient;
- a test step E3 to implement at least one eye test generated in the generation step E2. Test step E3 comprises at least:
  - a sub-step E3A of generation of instructions for the patient, implemented by the instruction generation system 12;
  - a sub-step E3B for ordering control unit 5 of automatic refractor 2 to take corrective lenses from reserve 6 and position them in the eyepieces 4A and 4B of eyepiece device 3;
  - a sub-step E3C for direct detection of indications in the form of gestures generated by the patient during the eye test, during which the patient looks at displays controlled by central unit 9 through eyepiece device 3 fitted with special corrective lenses and generates indications according to what they see, the sub-step E3C (implemented by the interface system 14) also comprising a direct transmission of these indications to central unit 9; and
- a processing step E4, implemented by central unit 9, and consisting of automatically determining the subjective ocular refraction of a patient, and preferably also a prescription, based in particular on the indications received. Processing step E4 preferably determines the subjective ocular refraction of the patient, using, among other things, the age of the patient, their objective ocular refraction RO measured by automatic refractometer 27, their optical range correction measured by the frontofocometer 29, and their responses collected by central unit 9 via interface system 14 during eye tests.

Steps E1 to E4 of the PR method are described in more detail below.

In the data input step E1, the patient inputs (using the data input unit 11) data about themselves, including age, which will be used by central unit 9 to determine subjective ocular refraction.

In a particular embodiment, the following can be envisaged:
- that the patient makes a pre-consultation payment, for example, using payment terminal 47; and/or
- that they enter other information about themselves such as their name and address for example, which may appear on the prescription.

In the data input step E1, in a preferred embodiment, the patient is also asked, via instruction generation system 12, to perform a measurement using automatic refractometer 27 to measure the objective ocular refraction RO of their eyes.

As an alternative, especially where device 1 is without an automatic refractometer 27, the patient can also be asked to enter (via the data input unit 11) the objective ocular refraction of their eyes if they know it.

In the data input step E1, in a preferred but not exclusive embodiment, the patient is also asked, via the instruction generation system 12, to place their spectacles in the frontofocometer 29 so that the latter automatically measures the lens corrections of their spectacles.

The subsequent generation step E2, implemented by the central unit 9, consists of automatically generating at least one eye test, using in particular the age of the patient, their objective ocular refraction RO and their optical correction range measured with a frontofocometer 29.

The eye test(s) are determined by central unit 9 to present different combinations of corrective lenses to the patient based on the objective ocular refraction RO. The patient looks at displays 25 controlled by central unit 9 through eyepiece device 3 fitted with these corrective lenses, and provides indications as to their vision via interface system 14 in test step E3.

Based on these patient indications, central unit 9 then determines an RB refraction (or fog refraction) and derives the subjective RF ocular refraction in processing step E4.

In a preferred embodiment, generation step E2 uses a fog test. Naturally, other types of tests can be carried out by device 1 in the context of the present invention.

Preferably, the fog test consists of making displays (viewed by the patient through the corrective lenses presented in eyepiece device 3) of letter Es, with branches of the E displayed in four different orientations, i.e. to the right, downwards, to the left and upwards. Four E's of different orientations are planned to be displayed, with the RO correction of the patient and E's of 2/10 in ocular device 3. The patient views these displays through the corrective lenses arranged in the ocular device 3. The vision is gradually brightened (and made possible) by gradually removing fog.

Preferably, with the fog technique, device 1 performs the test on only one eye to determine the RB refraction. By convention, the right eye is used, unless measurement with automatic refractometer 27 is impossible on the right eye.

In test step E3, to guide the patient, the instruction generation system 12 can emit (in sub-step E3A) the following voice message to the patient: "The following reading test is called the fog test. It is used to accurately determine your correction. Your vision will be deliberately blurred through the spectacles, and will then gradually become clearer. We will display letter Es with branches in four different orientations as follows. To the right, down, left and up. At the beginning, it will be totally impossible for you to respond and then we will gradually clear your vision by removing the fog. The most important thing for this test is to respond only when you can guess the direction of the E. When you do this, use the directional joystick to tell us the direction of the E, i.e. up, down, right, left". This directional joystick corresponds to joystick 25 described above.

By way of illustration, the method of calculation of the RB refraction is as follows, wherein the RB refraction is obtained starting from the RO refraction to which +4 dioptres are added.

The four possible E's are displayed, then corrective lenses of the RO+4 dioptre are integrated into the ocular device 3 of the automatic refractor. A single E of size 2/10 is displayed, and the orientation is changed after each response. In this case:
- if there is an error in the patient's response or if the patient cannot respond, 0.50 of fog is removed until we remove one dioptre of fog has been removed, then 0.25 is removed in steps;
- if four consecutive answers are correct, the test is stopped; similarly, if 2.75 is removed, the test is stopped.

Central unit 9 determines the RB refraction using the following expression: RB=refraction making it possible to read 2/10−1.25 (sphere dioptres).

Once the RB refraction has been determined for one eye, central unit 9 can either determine the RB refraction for the other eye in the same way or perform the following calculations:

determine an accommodation value Δ, using the following expression:

Δ=RB−RO on the tested eye; and remove this accommodation value Δ on the other eye without having testing it.

Finally, processing step E4, implemented by central unit 9, includes the automatic determination of the subjective ocular RF refraction.

Central unit 9 calculates the subjective ocular refraction RF from the RB refraction determined as described above.

To do this, central unit 9 takes into account the accommodation value Δ (such as Δ=RB−RO) of the patient, as follows, to determine the subjective ocular refraction RF:

if Δ=0, RF=RO=RB;

if Δ<1.00 dioptre, RF=RO+0.25;

if Δ≤1.00 dioptre, then:

if RB is sphere-positive, the RF value is determined from the RB value, taking into account a predetermined correspondence table between RB and RF values;

if RB is sphere-negative, a "red green" test is performed to determine the subjective ocular RF refraction.

Test step E4 also consists of generating a prescription P from this subjective RF ocular refraction. More specifically, central unit 9 determines the prescription P to be entered on the prescription, as follows:

if Δ=0 or if Δ<1.00 dioptre or if the patient is over 38 years of age:

if RF is sphere-negative, then P=RF as validated;

if RF is of positive sphere, then P=RF obtained from the correspondence table;

if Δ≥1.00 dioptre: P=RF.

Finally, the prescription P is provided to the patient, for example by being printed by print element 19. Prescription P can also be transmitted remotely to a third party, for example to a healthcare professional, using transmission element 21.

Device 1 can also be set up to issue an alert message advising the patient to consult an eye care professional in an emergency if their visual acuity is too low.

The method described above is therefore a method for the automated determination of the subjective ocular refraction of a patient, using an algorithm (integrated into central unit 9) and an analysis by artificial intelligence of the combination of objective refraction data measured automatically using, in particular, an automatic refractometer 27, the patient's age, their optical correction range measured using a frontofocometer 29 and their responses collected by central unit 9, wherein the various elements of the device 1 are controlled automatically by central unit 9, wherein central unit 9 presents in the eyepieces 4A and 4B of ocular device 3 a series of adapted corrective lenses, wherein the eye test(s) are implemented with vocal guidance of the patient by a synthesised voice (via the instruction generation system 12) and comprising a collection of responses using interface system 14.

The invention claimed is:

1. A device for automatic determination of at least a subjective ocular refraction of a patient, said device comprising:

a phoropter comprising an ocular device and a management unit configured to take corrective lenses from a reserve and position them in the ocular device;

a central unit configured to at least control the management unit of the phoropter in order to position corrective lenses in the ocular device; and a data input unit for inputting at least patient data into the central unit, an instruction generation system controlled by the central unit and configured to automatically generate instructions to the patient at least during an eye test;

an interface system between the patient and the central unit, which is configured to directly detect indications generated in the form of gestures by the patient at least during an eye test and to transmit these instructions directly to the central unit;

an autorefractor configured to measure the objective ocular refraction of the patient and to transmit the objective ocular refraction to the central unit; and a frontofocometer configured to measure corrections of the patient's eyeglass lenses and to transmit the measured corrections to the central unit, and wherein the central unit is configured to automatically implement at least one eye test in view of the objective ocular refraction from the autorefractor and the measured corrections from the frontofocometer by controlling the management unit and receiving the indications generated by the patient via the interface system to automatically determine:

an accommodation value from at least the received indications, the objective ocular refraction from the autorefractor, and the measured corrections from the frontofocometer;

the subjective ocular refraction from the accommodation value; and a prescription for spectacles for the patient adapted to the subjective ocular refraction, wherein, if:

the accommodation value is zero or less than an accommodation value threshold and the patient is sphere-negative, then the prescription equals the subjective ocular refraction determined from the accommodation value;

the accommodation value is zero or less than the accommodation value threshold and the patient is sphere-positive, then the prescription is determined from a correspondence table; and the accommodation value is greater than or equal to the accommodation value threshold, then the prescription equals the subjective ocular refraction determined from the accommodation value.

2. The device according to claim 1, wherein the central unit is configured to generate a prescription comprising a prescription for spectacles for the patient, adapted to said subjective ocular refraction.

3. The device according to claim 2, wherein the device further comprises at least one of the following elements:

a recording element configured to record the prescription; or a print element configured to print the prescription.

4. The device according to claim 2, wherein the device further comprises a transmission element configured to transmit the prescription remotely to a user.

5. The device according to claim 1, wherein the instruction-generating system comprises a voice transmission unit.

6. The device according to claim 1, wherein the interface system comprises at least one manual actuating element.

7. The device according to claim 1, wherein the interface system comprises at least one manual actuating element for detection of patient gestures.

8. The device according to claim 1, wherein the device comprises a local area network configured to allow communications between at least some of the phoropter, the central unit, the data input unit, the instruction generation system, the interface system, the autorefractor, and the frontofocometer.

9. The device according to claim 1, wherein at least some of the phoropter, the central unit, the data input unit, the instruction generation system, the interface system, the autorefractor, and the frontofocometer communicate with each other via serial links.

10. A booth for the automatic determination of the subjective ocular refraction of a patient, wherein the booth comprises at least one seat for a patient and the device according to claim 1.

11. The booth according to claim 10, wherein one or more of the phoropter, the central unit, the data input unit, the instruction generation system, the interface system, the autorefractor, and the frontofocometer are arranged so as to be accessible from the patient's seat.

12. The device according to claim 1, wherein the accommodation value threshold is 1.00 diopter.

13. The device according to claim 1, wherein, if:
the accommodation value is zero, then the subjective ocular refraction equals the objective ocular refraction;
the accommodation value is less than the accommodation value threshold, then the subjective ocular refraction equals the objective ocular refraction plus 0.25;
the accommodation value is greater than or equal to the accommodation value threshold and the patient is sphere-positive, then the subjective ocular refraction is determined from the correspondence table; and
the accommodation value is greater than or equal to the accommodation value threshold and the patient is sphere-negative, then the subjective ocular refraction is determined from a red-green duochrome test.

14. A method for the automatic determination of a subjective ocular refraction of a patient, using a device comprising:
a phoropter comprising an ocular device and a management unit configured to take corrective lenses from a reserve and position them in the ocular device;
a central unit;
a data input unit;
an instruction-generating system;
an interface system between the patient and the central unit;
an autorefractor configured to measure the objective ocular refraction of the patient; and
a frontofocometer configured to measure corrections of the patient's eyeglass lenses,
the method comprising:
a generation step, implemented by the central unit, and including automatic generation of at least one eye test using at least inputted data relating to the patient, the objective ocular refraction from the autorefractor, and the measured corrections from the frontofocometer;
a test step, including implementing at least one eye test generated in the generation step, the test step comprising at least:
a sub-step of generating instructions for the patient, implemented by the instruction-generating system;
a sub-step of directing the management unit of the automatic refractor to take corrective lenses from the reserve and position them in the ocular device; and
a sub-step of direct detection of indications generated in the form of gestures by the patient during the eye test, by viewing displays through the ocular device, and of direct transmission of these indications to the central unit, implemented by the interface system; and
a processing step, implemented by the central unit, and including automatic determination of:
at least an accommodation value of the patient from at least the indications received, the objective ocular refraction from the autorefractor, and the measured corrections from the frontofocometer;
the subjective ocular refraction from the accommodation value; and
a prescription for spectacles for the patient adapted to the subjective ocular refraction, wherein, if:
the accommodation value is zero or less than an accommodation value threshold and the patient is sphere-negative, then the prescription equals the subjective ocular refraction determined from the accommodation value;
the accommodation value is zero or less than the accommodation value threshold and the patient is sphere-positive, then the prescription is determined from a correspondence table; and
the accommodation value is greater than or equal to the accommodation value threshold, then the prescription equals the subjective ocular refraction determined from the accommodation value.

15. The method according to claim 14, wherein the method further comprises at least one data input step which is implemented prior to the generation step.

16. The method according to claim 14, wherein the generation step and the test step use a fog test.

17. The method according to claim 14, wherein the test step consists of displaying letter Es with branches having different orientations.

18. The method according to claim 14, wherein the accommodation value threshold is 1.00 diopter.

19. The method according to claim 14, wherein, if:
the accommodation value is zero, then the subjective ocular refraction equals the objective ocular refraction;
the accommodation value is less than the accommodation value threshold, then the subjective ocular refraction equals the objective ocular refraction plus 0.25;
the accommodation value is greater than or equal to the accommodation value threshold and the patient is sphere-positive, then the subjective ocular refraction is determined from a correspondence table; and
the accommodation value is greater than or equal to the accommodation value threshold and the patient is sphere-negative, then the subjective ocular refraction is determined from a red-green duochrome test.

* * * * *